(12) United States Patent
Loose et al.

(10) Patent No.: US 11,508,475 B2
(45) Date of Patent: Nov. 22, 2022

(54) METHOD FOR ASSIGNING A MEDICAL DEVICE FROM A DATA NETWORK TO A LOCATION AS WELL AS DEVICE FOR A DATA NETWORK

(71) Applicant: Drägerwerk AG & Co. KGaA, Lübeck (DE)

(72) Inventors: Alexander Loose, Reinfeld (DE); Stephan Pöhlsen, Lübeck (DE); Stefan Schlichting, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1663 days.

(21) Appl. No.: 15/381,994

(22) Filed: Dec. 16, 2016

(65) Prior Publication Data

US 2017/0177817 A1    Jun. 22, 2017

(30) Foreign Application Priority Data

Dec. 18, 2015   (DE) ..................... 10 2015 016 403.1

(51) Int. Cl.
*G16H 40/63*          (2018.01)
*H04W 4/38*           (2018.01)
(Continued)

(52) U.S. Cl.
CPC ............ *G16H 40/63* (2018.01); *G16Z 99/00* (2019.02); *H04L 67/12* (2013.01); *H04W 4/08* (2013.01); *H04W 4/38* (2018.02)

(58) Field of Classification Search
CPC ........ G16H 10/00; G16H 10/40; G16H 15/00; G16H 20/00; G16H 20/10; G16H 20/13;
(Continued)

(56) References Cited

U.S. PATENT DOCUMENTS

2003/0105389 A1*  6/2003  Noonan ................. G16H 40/67
                                                      600/300
2005/0135306 A1*  6/2005  McAllen ................. H04L 67/14
                                                      370/329

(Continued)

OTHER PUBLICATIONS

Valentim et al. 2008 A, "MP-HA: Multicycles Protocol for Hospital Automation over multicast with IEEE 802.3," 2008 6th IEEE International Conference on Industrial Informatics, Daejeon, 2008, pp. 979-984, doi: 10.1109/INDIN.2008.4618244.*
(Continued)

*Primary Examiner* — Robert W Morgan
*Assistant Examiner* — Charles P Coleman
(74) *Attorney, Agent, or Firm* — McGlew and Tuttle, P.C.

(57) ABSTRACT

A method, assigning a medical device from a data network to a location, includes: receiving a group message, having a medical device data network address; providing a first data set, indicating network addresses of active network components; and sending request messages to active network components, indicating a data network address thereof and data network address of the medical device. An acknowledgment message from a defined active network component indicates the data network address and a port identity thereof and data network address of the medical device. A second data set is provided indicating an assignment of tuples of active component data network addresses and port identities to locations. The medical device is assigned a location based on the second data set, the data network address of the defined active component and the indicated port identity. An assignment data set is provided indicating an assignment of medical device to assigned location.

17 Claims, 3 Drawing Sheets

(51) Int. Cl.
*H04W 4/08* (2009.01)
*G16Z 99/00* (2019.01)
*H04L 67/12* (2022.01)

(58) Field of Classification Search
CPC ........ G16H 20/17; G16H 30/00; G16H 40/00; G16H 50/00; G16H 70/00; G16H 80/00; G16H 40/63; H04L 67/12
USPC .................................................. 705/2, 3, 20
See application file for complete search history.

(56) References Cited

U.S. PATENT DOCUMENTS

| | | | | |
|---|---|---|---|---|
| 2005/0138428 A1* | 6/2005 | McAllen | ................ | G16H 40/20 |
| | | | | 726/4 |
| 2008/0191866 A1* | 8/2008 | Falck | ................... | A61B 5/0006 |
| | | | | 340/539.12 |
| 2011/0187526 A1* | 8/2011 | Weiner | ..................... | G08B 1/08 |
| | | | | 340/539.13 |
| 2013/0254348 A1* | 9/2013 | Mass | .................. | H04L 65/1069 |
| | | | | 709/219 |
| 2016/0080211 A1* | 3/2016 | Anand | .................. | G06F 16/285 |
| | | | | 709/224 |
| 2016/0080212 A1* | 3/2016 | Ramachandran | ..... | G06F 16/285 |
| | | | | 370/338 |
| 2017/0177817 A1* | 6/2017 | Loose | ................... | G16H 40/63 |

OTHER PUBLICATIONS

Valentim et al. 2008 B, "Medium access control: Multicycles Protocol for Hospital Automation over multicast with IEEE 802.3," 2008 34th Annual Conference of IEEE Industrial Electronics, Orlando, FL, 2008, pp. 1493-1498, doi: 10.1109/IECON.2008.4758174.*

Sebestyen et al. 2010, "Remote monitoring of patients with mobile healthcare devices," 2010 IEEE International Conference on Automation, Quality and Testing, Robotics (AQTR), Cluj-Napoca, 2010, pp. 1-6, doi: 10.1109/AQTR.2010.5520793.*

Parziale et al., TCP/IP Tutorial and Technical Overview, Dec. 19, 2006.*

Rooney, IP Address Management: Principles and Practice, 2011.*

Cisco 300 Series Stackable Managed Switches Command Line Interface Reference Guide, Chapter 22, Release 1.4, 2014 Cisco Systems, Inc.

* cited by examiner

METHOD FOR ASSIGNING A MEDICAL DEVICE FROM A DATA NETWORK TO A LOCATION AS WELL AS DEVICE FOR A DATA NETWORK

CROSS REFERENCE TO RELATED APPLICATIONS

This application claims the benefit of priority under 35 U.S.C. § 119 of German Application 10 2015 016 403.1, filed Dec. 18, 2015, the entire contents of which are incorporated herein by reference.

FIELD OF THE INVENTION

The present invention relates to medical devices, which have a data network interface for transferring such patient-related data as, e.g., physiological values of a patient across a network to a central network entity, for example, a server.

BACKGROUND OF THE INVENTION

Medical devices, which have a data network interface for transferring such patient-related data as, e.g., physiological values of a patient across a network to a central network entity, for example, a server, are known from the state of the art. In this case, it is occasionally necessary in such a central entity to know at which physical location (e.g., bed of a hospital ward) a defined medical device is located. This is necessary in order to then assign the provided data of the medical device to a physical location of the patient or else to a defined patient. Such an assignment may likewise be displayed, for example, within the framework of a visual display or a display of patient data in order to inform the clinical staff about to which physical location or else to which patient the displayed data belong.

Methods, in which the location data are inputted directly into the medical device, for example, by means of an input at the medical device when positioning the medical device at the physical location, are known in this connection from the state of the art. The medical device may then additionally provide this location data within the framework of providing physiological patient data.

A method, in which a patient monitor is located as a medical device with regard to its location by a central network unit having a data set, which indicates respective locations of respective network switches and wherein a central unit can determine to which network switching unit the patient monitor is connected by means of a data protocol and exchange of data messages, is known from US 2011/0187526 A1.

SUMMARY OF THE INVENTION

An object of the present invention is to provide an assignment of a medical device to a physical location in an automated manner.

The method according to the present invention for assigning a medical device from a data network to a physical location has the steps: Receiving a group message, which has a data network address of the medical device; providing a first data set, which indicates respective data network addresses of respective active network components of the data network; sending respective request messages to the respective active network components, wherein a respective request message indicates a respective data network address of the respective active network component and the data network address of the medical device; receiving an acknowledgment message from a defined active network component, which indicates the data network address of the defined active network component, a port identity of a port of the defined active network component and the data network address of the medical device; providing a second data set, which indicates an assignment of respective tuples of active network component data network addresses and port identities to respective locations; assigning the medical device to a location on the basis of the second data set as well as the data network address of the defined active network component and of the indicated port identity; as well as further providing an assignment data set, which indicates an assignment of the medical device to the assigned location. Furthermore, the second data set indicates an assignment of the respective tuples of active network component data network addresses and port identities to respective patient data sets, which identify patients, wherein the medical device is further assigned to a patient data set on the basis of the second data set, and wherein the assignment data set has, further, the assigned patient data set.

In the sense of the present application, an active network component is a router or a managed switch or a multilayer switch.

The method according to the present invention is advantageous because only an assignment of a physical location to a defined port or to a port identity of an active network component has to be present or be provided in order to be able to then assign the medical device to the physical location in an automated manner.

In a clinical setting, provisions are usually made for an active network component, e.g., a router or a managed switch, which has a plurality of respective ports, to which respective medical devices can be connected, to be present, for example, in a hospital room. In this connection, defined ports for the connection of medical devices to defined physical locations are provided. For example, defined ports are provided for the connection of medical devices for a particular hospital bed. An active network component such as a router or a managed switch can thus provide one or more hospital beds with a network connection in a setting such as a hospital room.

By providing data, in the form of the second data set, about which port of which active network component is assigned to a defined physical location, it can be determined at which physical location the medical device is located in an automated manner by the method according to the present invention or by the device according to the present invention. To this end, it is only necessary for the medical device to send a group message into the data network, wherein the message must simply only indicate the identity of the medical device. The assignment of the medical device to the physical location can then take place by the exchange of the other messages in the course of the suggested method.

A group message in the sense of the present application is a data network message. Such a group message as data network message is sent to one or more network units of a group of network units. The group of network units is then preferably defined by group identification data, e.g., a multicast address or a quantity of a plurality of respective data network addresses of respective network units, which quantity is predefined by means of a separate data set.

A group message in the sense of the present application is thus a data network message of the type of a broadcast message, an anycast message, a multicast message or one or more unicast messages.

In conventional methods, in which data concerning the physical location of the device are inputted into the medical device, for example, by means of an input at the medical device, the clinical staff is entrusted with this input and is thus required in the staffs work load. This is avoided by the method according to the present invention and the device according to the present invention.

In case of other possible scenarios of an assignment of a medical device to a location, for example, a barcode, which is positioned on the medical device, as well as a second barcode, which is located at the physical location, is scanned, wherein the scanning unit then transmits the pooling of the data of the barcode to a central network unit, so that the central unit is then informed about the physical location of the medical device. In this case as well, the clinical staff has to perform this scanning operation. Such a work load of the clinical staff is also avoided by the method according to the present invention and the device according to the present invention.

Before receiving the group message, which has the data network address of the medical device, the method preferably has a step of sending a group message, which indicates a request to medical devices for them to send their own respective group messages, which indicate their own respective data network addresses. This configuration of the present invention is advantageous because the medical device itself does not have to determine at which time it sends the group message, which has the data network address of the medical device. This sending of the group message, which has the data network address of the medical device, may then be performed by the medical device when it receives the group message, which indicates a request to the medical device to send its respective one group message. Consequently, it remains in the hand of the central device for the data network to decide when a medical device reports a group message to the central device.

The assignment data set preferably contains identification data of the medical device as well as also a data set, which identifies the location. Consequently, the provided data set can be used directly by another unit and the identification data as well as the data set, which identifies the location, can be accessed.

The identification data of the medical device are preferably the data network address of the medical device. This is advantageous since such data network addresses within a data network are usually assigned unambiguously, so that even the data network address can be used as identification data of the medical device.

According to the present invention, the second data set further indicates an assignment of respective tuples of active network component data network addresses and port identities to respective patient data sets, which identify patients, wherein the medical device is then further assigned to a patient data set on the basis of the second data set, wherein the assignment data set also has the assigned patient data set. This is advantageous because not only an assignment of the medical device to a physical location, but also to the patient data is performed in an automated manner. Thus, the assignment data set can be used to determine an assignment of the medical device to the patient directly.

The provision of the assignment data set preferably comprises the sending of a data message to the medical device, wherein the data message contains the assignment data set. This configuration of the present invention is advantageous because the medical device is informed, as a result, about which is its physical location and possibly also about to which patient it is to be assigned. For its part, the medical device may then possibly in the course of a sending of physiological patient data indicate its location at the same time as well, so that another unit, which receives all these data, is then indirectly or directly informed about to which physical location and also possibly to which patient these sent physiological data are to be assigned.

The provision of the assignment data set preferably comprises the sending of a data message to a server unit, wherein the data message contains the assignment data set. This configuration of the present invention is advantageous because the server is thus informed about which medical device is to be assigned to which physical location and possibly to which patient as well, so that an assignment of physical location and possibly of patient to medical devices in the server unit can be recorded by simple reading of the data message and may possibly be used in the course of other applications.

The sending of the data message to the server unit preferably takes place upon receiving a request message at the server unit. This is advantageous because the sending of the data message to the server unit does not have to take place immediately and also not absolutely periodically, but only upon receipt of the request message. A reduction of the data volume arising in the data network is thus achieved.

The method is preferably executed with computer program means (a computer program configuration) on at least one processing unit. This is advantageous because such an implementation of computer program means, i.e., software, on one or more processing unit makes possible an economic implementation of the method.

Further, a device for a data network is suggested, having at least one data network interface for receiving and for sending data network messages; at least one memory unit; at least one processing unit, wherein the memory unit is configured to provide a first data set, which indicates respective data network addresses of respective active network components of the data network; and a second data set, which indicates an assignment of respective tuples of active network component data network addresses and port identities to respective locations, wherein the processing unit using the data network interface is configured to receive a group message, which has a data network address of the medical device, to send respective request messages to the respective router of the first data set, wherein a respective request message indicates a respective data network address of the respective active network component and the data network address of the medical device, to receive an acknowledgment message from a defined active network component, which indicates the data network address of the defined active network component, a port identity of a port of the defined active network component and the data network address of the medical device, to assign the medical device to a location on the basis of the second data set as well as of the data network address of the defined router and of the indicated port identity as well as further to provide an assignment data set, which indicates an assignment of the medical device to the assigned location. Furthermore, it, the second data set, indicates an assignment of the respective tuples of active network component data network addresses and port identities to respective patient data sets, which identify patients, wherein the medical device is further assigned to a patient data set on the basis of the second data set, and wherein the assignment data set has, further, the assigned patient data set.

Advantages of the suggested method likewise apply to the suggested device. These advantages likewise apply to the implementation of the method according to the present invention with computer program means on at least one processing unit.

The present invention is explained in greater detail below on the basis of the figures on the basis of special embodiments without limiting the general idea of the invention. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
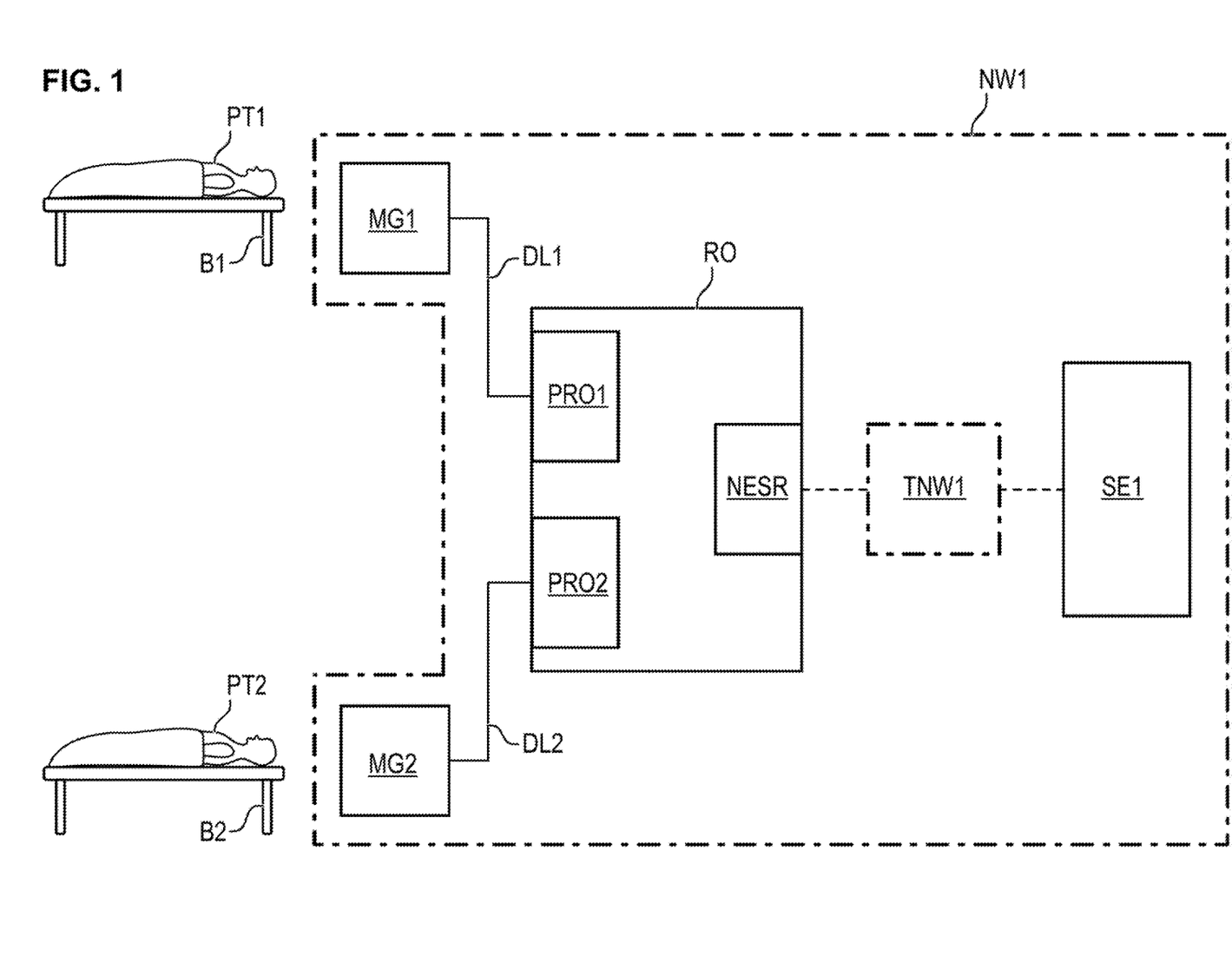
FIG. 1 is a schematic view showing a network connection of medical devices to a central network unit.

Referring to the drawings, FIG. 1 shows a scenario, in which respective patients PT1, PT2 are located at respective physical locations in the form of their respective beds B1, B2. Each patient PT1, PT2 is provided, in this example, with a respective medical device MG1, MG2, which is each connected via a respective wired data line DL1, DL2 to a respective active network component in the form of a router RO. In this case, each medical device MG1, MG2 is connected to one of the own respective ports PRO1, PRO2, of the router RO. The router RO has, further, a network interface NESR, by means of which it can communicate with a central unit, for example, a server, SE1, via a subnetwork TNW1. The communication units shown here MG1, MG2, RO as well as SE1 and the subnetwork TNW1 form a data network NW1. Instead of the router RO, a managed switch or a multilayer switch is possible as an active network component as well.

If a medical device MG1, MG2 provides respective patient data of respective patients PT1, PT2 to the server unit SE1 via the data network NW1, then the server unit SE1 has to know which medical device MG1, MG2 is to be assigned to which physical location B1, B2.

The server unit SE1 shall preferably also know to which patient PT1, PT2 a respective medical device MG1, MG2 is to be assigned. To this end, methods already mentioned above may be performed by applying the work effort of the clinical staff.

A mode of operation of the method according to the present invention shall now be explained in greater detail with reference to FIG. 2.

Figure 2:
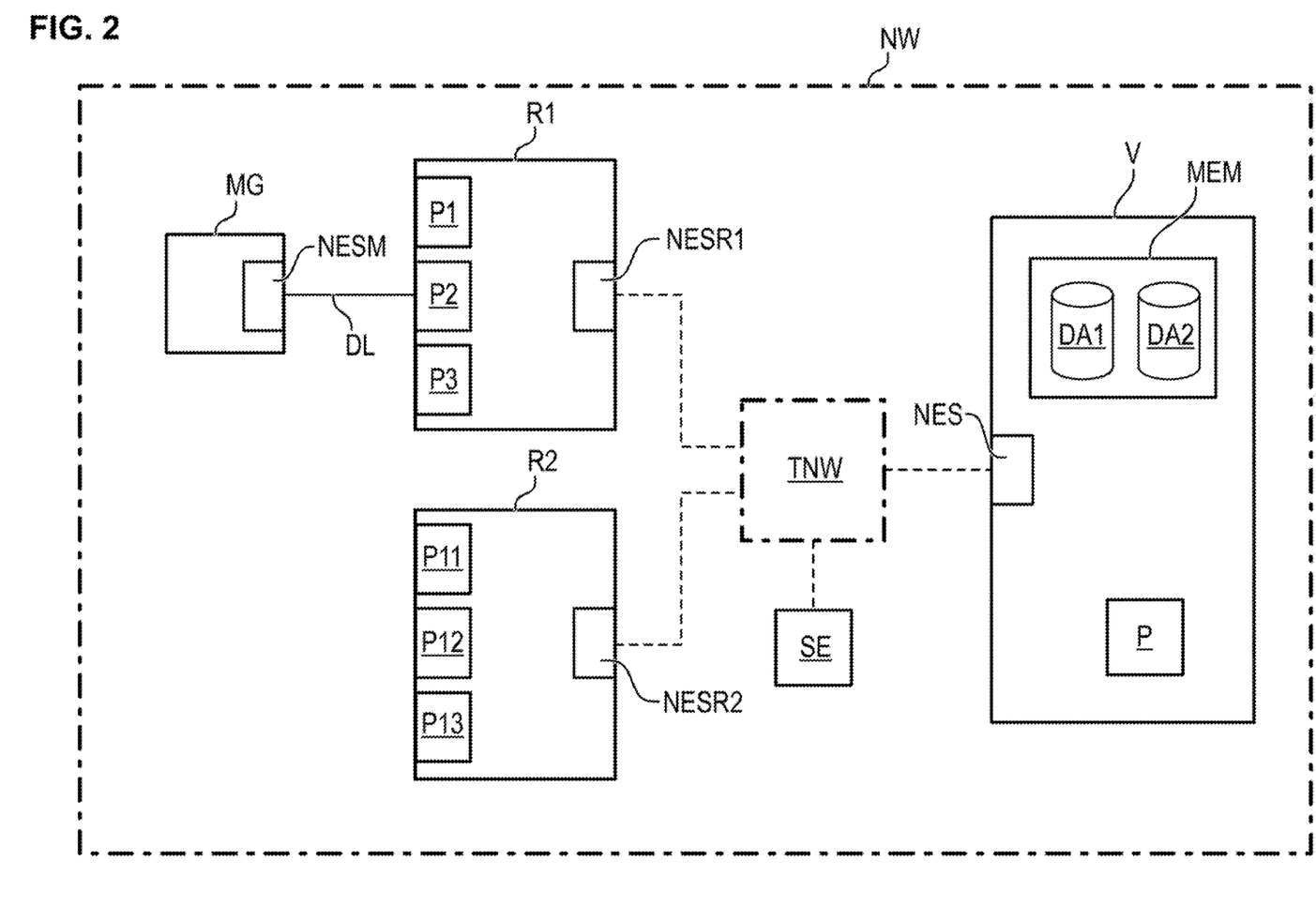
FIG. 2 is a schematic view showing a data network with a device according to the present invention.

FIG. 2 shows a data network NW, in which a medical device MG is located, which is connected to a port P2 of an active network component in the form of a router R1 directly via a data line DL. This data line DL is preferably a LAN cable. The medical device MG has a data network interface NESM. Instead of a router R1, a managed switch or a multilayer switch is also possible as an active network component.

The router R1 has a variety of ports P1, P2, P3. Such ports P1, P2, P3 are possibly assigned to defined physical locations for medical devices. Thus, provisions are possibly made in a clinical setting for a medical device MG to be able to be connected only to a defined port P2 of a router R1 at a defined physical location. The router R1 has a data network interface NESR1 to a subnetwork TNW.

A second exemplary active network component in the form of a router R2 with respective ports P11, P12, P13 and its own data network interface NESR2 for communication to the subnetwork TNW is, further, shown. Instead of a router R02, a managed switch or a multilayer switch is also possible as an active network component.

Further, a server unit SE is shown, which is connected to the subnetwork TNW.

The device V according to the present invention has at least one data network interface NES for receiving or sending data network messages. Further, the device V has at least one processing unit P. Further, the device V has at least one memory unit MEM. The processing unit P is configured to receive and to send a variety of data messages using the data network interface NES.

The memory unit MEM provides a first data set DA1, which indicates respective data network addresses of respective active network components of the data network, which shall still be explained later in greater detail with reference to FIG. 3.

Further, the memory unit MEM provides a second data set DA2, which indicates an assignment of respective tuples of a respective active network component data network address and a respective port identity to a respective physical location. This shall also be explained later in greater detail with reference to FIG. 3.

The device V performs a method according to the present invention in order to bring about an assignment of the medical device MG to a physical location.

Figure 3:
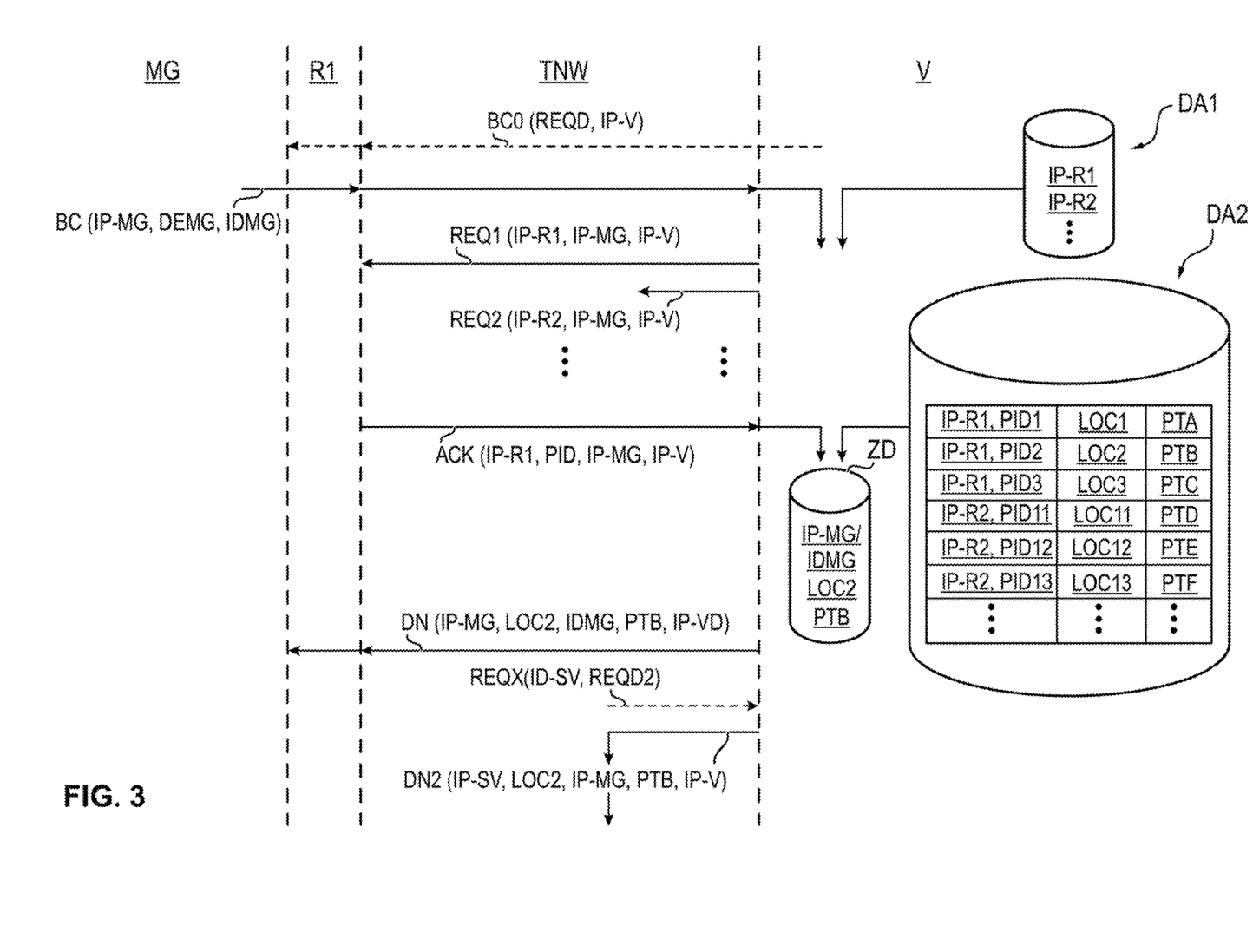
FIG. 3 is a schematic view showing data network messages, which are used in the course of the method according to the present invention.

FIG. 3 shows a sequence of an exchange of data network messages in the course of the method according to the present invention.

The medical device MG is represented on the left-hand side, wherein the router R1 (active network component) is located next as a communication path from the device MG to the subnetwork TNW, wherein then continuing further behind the router R1, the subnetwork TNW represents a connection to the device V according to the present invention. The communication in the network NW takes place, for example, via the known IP technology using known routing protocols as well as known IP messages.

The medical device MG sends a group message BC, which has a data network address IP-MG, and preferably in the form of an IP address, of the medical device. Further, the group message BC has preferably a data element DEMG, which indicates that the group message BC was sent from a medical device MG. The group message preferably has, further, identification data IDMG, which unambiguously identify the medical device MG. These identification data IDMG do not necessarily have to be contained in the group message BC in order to use these later as identification data of the medical device; instead, the data network address IP-MG of the medical device MG may also be used later as identification data.

A group message BC in the sense of the present application is a data network message. Such a group message as a data network message is sent to one or more network units of a group of network units. The group of network units is then preferably defined by group identification data, e.g., a multicast address or a quantity of a plurality of respective data network addresses of respective network units, which quantity is predefined by means of a separate data set.

A group message in the sense of the present application is thus a data network message of the type of a broadcast message, an anycast message, a multicast message or one or more unicast messages.

The group message BC is a broadcast message BC in this example.

The group message BC is as a group message via the router R1 and the subnetwork TNW to the device V.

The sending of the group message BC from the medical device MG may preferably take place in case the medical device MG has first received its data network address IP-MG. Such a receipt of a data network address IP-MG may be brought about, for example, by the medical device MG executing the DHCP protocol in an IP network.

The sending of the group message BC by the medical device may also take place in case the medical device MG has received a new IP address within the framework of a reallocation of IP addresses.

As an alternative to this, the sending of the group message BC may be carried out by the medical device MG if the medical device MG has received a request message BC0 beforehand. Thus, before receiving the group message BC, the device V according to the present invention may send its own group message BC0, in the form of a broadcast message in this example, which indicates a request to medical devices MG to send their own respective group messages BC, which indicate their own respective data network addresses IP-MG. In this connection, a group message BC0 has at least one data element REQD, which indicates this request. Optionally, the group message BC0 has the sender address IP-V as the data network address of the device V.

A first data set DA1 is provided to the device V. This data set DA1 indicates respective data network addresses IP-R1, IP-R2 of respective routers or active network components of the data network. These data network addresses IP-R1, IP-R2 may be pooled in the device V by using usual protocols for obtaining topology data of the data network and then even be provided by the device V in the data set DA1. The data set DA1 is preferably a data set provided to the device V beforehand.

The device V sends respective request messages REQ1, REQ2 to those routers R1, R2, which are indicated in the first data set DA1. A respective request message REQ1, REQ2 indicates a respective data network address IP-R1, IP-R2 of the respective router R1, R2 as well as the data network address IP-MG of the medical device MG. The request message REQ1, REQ2 preferably has, further, the sender address IP-V as the data network address of the device V.

If the corresponding request message REQ1, which is to the router R1, is now received at the router R1, then the router R1 determines, at which defined port P2 the medical device MG is connected to the router.

The router may carry out this determination of the defined port P2, for example, upon receiving the message REQ1. As an alternative, the router may carry out this determination beforehand and store the port assignment information thus obtained temporarily in a data set or a table. In this alternative embodiment, the determination is thus carried out by reading the port assignment information from the data set or the table.

For determining a port identity of a port in relation to a network device, i.e., the medical device, a variety of methods and protocols, which an active network component, i.e., a router or a managed switch or multilayer switch, can execute, are known from the state of the art. For this, for example, the Address Resolution Protocol (ARP), among others, may be accessed. For the example of a managed switch of an IP network, the port identity can be determined by using corresponding commands or messages as described in the document "Cisco 300 Series Stackable Managed Switches Command Line Interface Reference Guide, Chapter 22, Release 1.4, 2014 Cisco Systems, Inc." http://www.cisco.com/c/dam/en/us/td/docs/switches/lan/csbms/sf30x_sg30x/administration_guide/CLI_300.pdf.

After determining the port identity, the router R1 sends an acknowledgment message ACK to the device V. The acknowledgment message ACK indicates the data network address IP-R1 of the router R1, a port identity PID of the port of the router R1, to which the medical device MG is connected as well as the data network address IP-MG of the medical device MG. Further, the message ACK has the target address IP-V as the data network address of the device V.

A second data set DA2 is provided to the device V. The data set DA2 indicates an assignment of respective tuples of a respective router data network address or of a respective active network component data network address and of a respective port identity to a respective location. For example, a tuple of the router data network address IP-R1 and of the port identity PID1 is indicated to the location information LOC1. The data set DA2 preferably has, further, patient data sets PTA, . . . , PTF, which likewise are assigned to a tuple of an active network component network address or router data network address IP-R1 and of a port identity PID1.

Corresponding other tuples, such as, for example, the tuple IP-R2, PID11, are thus also assigned to a physical location LOC11 as well as preferably patient data PTD.

An assignment of the medical device to a physical location then takes place on the basis of the second data set DA2 as well as the data network address IP-R1 of the router R1 and the indicated port identity PID. An assignment data set ZD, in which, for example, the data network address IP-MG is contained as identification data, is thus generated; further, a data set LOC2, which indicates the location of the medical device MG, is contained in the data ZD. The assignment data set ZD preferably has, further, the identity IDMG of the medical device MG as identification data, which were preferably sent within the framework of the group message BC beforehand by the medical device MG to the device V, and which the device V preferably stores there for processing.

It is likewise possible that in addition to the location information LOC2, the assignment data set ZD has only the identification data IDMG and not the data network address IP-MG of the medical device MG as identification data.

The assignment data set ZD has, further, the patient data PTB.

The medical device MG is thus assigned on the basis of the second data set DA2 to a patient data set PTB, so that the assignment data set ZD also has the patient data set PTB.

The assignment data set ZD is, in other words, a data set, which indicates an assignment of the medical device MG to a physical location LOC2.

The assignment mentioned here thus takes place by comparing and checking for agreement of a combination of the data network address IP-R1 of the router R1 and the port identity PID with corresponding tuples from the data set DA2.

The assignment data set ZD is then provided to the device V.

The provision preferably comprises the sending of a data message DN to the medical device MG, wherein the data message DN contains the assignment data set ZD.

The data message DN is directed to the medical device MG and thus contains the data network address IP-MG of the medical device MG as well as at least also the data set LOC2 as location information, which identifies the physical location, as the target network address. Further, the data message DN, as the above-mentioned assignment data set ZD, preferably has the identification data IDMG of the medical device MG as well as the patient data set PTB. The data message DN has the data network address IP-V of the device V sending the message DN as sender address.

After receiving the data message MG, the medical device may itself then have data LOC2 with regard to its physical location and likewise provide these data then, e.g., within the framework of a provision of physiological patient data to other units, for example, the central server unit SE from FIG. 2.

A data message DN2 is preferably sent to the server unit SE by the device V, wherein the message likewise contains the assignment data set ZD. The structure of the data message DN2 is hence up to the target address IP-SV identical to the structure of the data message DN at the medical device MG.

The sending of the data message DN2 to the server unit SE from FIG. 2 preferably takes place upon receipt of a request message REQX. Such a request message REQX from a server unit SE from FIG. 2 has a data element REQD2, which indicates that the device V shall send the data message DN2 to the server unit SE. Consequently, a query of assignment of medical devices to physical locations by the server unit to the device V is made possible.

The method is preferably executed with computer program means on at least one processing unit from FIG. 2.

The device V from FIG. 2 is thus correspondingly configured to execute the method according to the present invention with its data network interface NES, its memory unit MEM as well as its processing unit P.

Even though some aspects were described in connection with a device, it is understood that these aspects also represent a description of the corresponding method, so that a block or a component of a device is also defined as a corresponding method step or as a feature of a process step. In analogy thereto, aspects, which were described in connection with a method step or as a method step, also represent a description of a corresponding block/step or detail or feature of a corresponding device, or that the device or the corresponding processing unit is configured to execute the method step.

The suggested processing unit shall be considered to be at least one processing unit. An implementation of the at least one processing unit may also be achieved by a combination of a plurality of processing units, preferably by using software in conjunction with hardware. Depending on defined implementation requirements, exemplary embodiments of the present invention may be implemented in hardware and/or in software. The implementation may be carried out by using a digital storage medium, for example, a floppy disk, a DVD, a Blu-Ray Disc, a CD, an ROM, a PROM, an EPROM, an EEPROM or a FLASH memory, a hard drive or another magnetic or optical memory, on which electronically readable control signals are stored, which can interact or do interact with a programmable hardware component such that the respective method is executed.

A programmable hardware component may be formed by a processor, a computer processor (CPU=Central Processing Unit), a graphics processor (GPU=Graphics Processing Unit), a computer, a computer system, an application-specific integrated circuit (ASIC), an integrated circuit (IC), a one-chip system (SOC=System on Chip), a programmable logic element or a field programmable gate array (FPGA) with a microprocessor.

The digital storage medium may therefore be machine- or computer-readable. Some exemplary embodiments thus comprise a data carrier, which has electronically readable control signals, which are able to interact with a programmable computer system or a programmable hardware component such that one of the methods described herein is executed. An exemplary embodiment is thus a data carrier (or a digital storage medium or a computer-readable medium), on which the program for executing one of the methods described herein is recorded.

Exemplary embodiments of the present invention can generally be implemented as a program, firmware, computer program or computer program product with a program code or as data, wherein the program code or the data is or are operative to execute one of the methods when the program runs on a processor or a programmable hardware component. The program code or the data may, for example, be stored on a machine-readable carrier or data carrier. The program code or the data may be present as a source code, machine code or byte code as well as another intermediate code, among others.

Another exemplary embodiment is, further, a data stream, a signal sequence or a sequence of signals, which represents the program for executing one of the methods described herein. The data stream, the signal sequence or the sequence of signals may, for example, be configured to that effect to be transferred via a data communication link, for example, via the internet or another network. Exemplary embodiments are thus also signal sequences representing data, which are suitable for a transmission via a network or a data communication link, wherein the data represent the program.

A program according to an exemplary embodiment may implement one of the methods during its execution, for example, by reading these storage locations or writing a datum or a plurality of data into same, as a result of which possibly switching operations or other operations in transistor structures, in amplifier structures or in other electric, optical, magnetic components or components operating according to another operating principle are brought about. Correspondingly, by reading a storage location, data, values, sensor values or other data can be collected, determined or measured by a program. A program may hence collect, determine or measure variables, values, measured variables and other data by reading one or a plurality of storage locations, as well as bring about, cause or execute an action as well as activate other devices, machines and components by writing into one or a plurality of storage locations.

While specific embodiments of the invention have been shown and described in detail to illustrate the application of the principles of the invention, it will be understood that the invention may be embodied otherwise without departing from such principles.

APPENDIX

List of Reference Characters

| | |
|---|---|
| Acknowledgment message | ACK |
| Bed | B1, B2 |
| Group message | BC, BC0 |
| Data set | DA1, DA2 |
| Data element | DEMG |
| Data line | DL, DL1, DL2 |
| Data message | DN, DN2 |
| Identification data | IDMG |
| Data network addresses | IP-R1, IP-R2, IP-MG |
| Target address | IP-SV |
| Sender address | IP-V |
| Location information | LOC1, . . . , LOC3, LOC11, . . . , LOC13 |
| Memory unit | MEM |
| Medical device | MG, MG1, MG2 |
| Network interface | NESR, NESM, NESR1, NESR2, NES |
| Data network | NW1 |
| Processing unit | P |
| Port identity | PID, PID1, . . . , PID3, PID11, . . . , PID13 |
| Port | PRO1, PRO2, P1, P2, P3, P11, P12, P13 |
| Patient | PT1, PT2 |
| Patient data sets | PTA, . . . , PTF |
| Request messages | REQ1, REQ2 |
| Data element | REQD, REQD2 |
| Request message | REQX |
| Active network component | RO, R1, R2 |
| Server | SE1, SE |
| Subnetwork | TNW1, TNW |
| Device | V |
| Assignment data set | ZD |

What is claimed is:

1. A method for assigning a medical device from a data network to a physical location, the method comprising the steps of:
providing a data network device comprising: at least one data network interface connecting the data network device to the data network, the data interface receiving and sending data network messages; a memory unit configured to provide data sets and at least one processing unit connected to the memory unit and using the data network interface;
receiving a group message at the data network device, the group message comprising a data network address of the medical device sending the group message;
providing a first data set in the memory of the data network device, which indicates respective data network addresses of respective active network components of the data network;
sending respective request messages from the data network device to the respective active network components of the first data set, wherein each respective request message indicates a respective data network address of the respective active network component and the data network address of the medical device that sent the group message;
receiving an acknowledgment message from a defined active network component, which defined active network component received the request message, which acknowledgment message indicates the data network address of the defined active network component, a port identity of a port of the defined active network component, to which the medical device is connected and the data network address of the medical device;
providing a second data set in the memory of the data network device including assigning active network component data network addresses and port identities to respective physical locations and assigning port identities to respective patient data sets, which identify patients such that the second data set in the memory of the data network device indicates an assignment of respective tuples of active network component data network addresses and port identities to respective physical locations and further indicates an assignment of the respective tuples of active network component data network addresses and port identities to respective patient data sets, which identify patients;
with the processor of the data network device, assigning the medical device to a physical location on a basis of the received acknowledgment message and the data network address of the defined active network component and of the indicated port identity assigned to the physical location from the second data set;
with the processor of the data network device, providing an assignment data set, which indicates the assignment of the medical device to the assigned physical location;
with the processor of the data network device, further assigning the medical device to a patient data set on the basis the received acknowledgment message and the data network address of the defined active network component and of the indicated port identity assigned to the patient data set from the second data set, wherein the assignment data set further comprises the assigned patient data set, which identifies a patient.

2. A method in accordance with claim 1, further comprising the step of sending a group message from the data network device over the data network via the network interface, which group message indicates a request to medical devices connected to the data network to send their own respective group messages, which indicate their own respective data network addresses, wherein the sending of the group message by the data network device occurs before receiving the group message by the data network device, which has the data network address of the medical device.

3. A method in accordance with claim 1, wherein the assignment data set contains identification data of the medical device as well as, further, a data set, which identifies the assigned physical location.

4. A method in accordance with claim 3, wherein the identification data of the medical device is the data network address of the medical device.

5. A method in accordance with claim 1, wherein the provision of the assignment data set comprises sending a data message from the data network device to the medical device via the data network, wherein the data message contains the assignment data set.

6. A method in accordance with claim 1, wherein the provision of the assignment data set comprises sending a data message to a server unit, wherein the data message contains the assignment data set.

7. A method in accordance with claim 6, wherein the sending of the data message takes place upon receipt of a request message to the server unit.

8. A method in accordance with claim 1, wherein the method is executed with a computer program means on at least one processing unit.

9. A device for a data network having one or more active network components and one or more network connected medical devices, each of the one or more medical devices being connected to a port of one of the active network components, the device comprising:
a data network interface connecting the data network device to the data network, the data network interface receiving and sending data network messages;

a memory unit configured to provide a first data set, which indicates respective data network addresses of respective active network components of the data network, and a second data set, which indicates an assignment of respective tuples of active network component data network addresses and active network component port identities to respective physical locations as well as an assignment of the respective tuples of active network component data network addresses and port identities to respective patient data sets, which identify patients; and a processing unit connected to the memory unit and using the data network interface and configured to:

receive a group message at the data network device, which group message has a data network address of a medical device sending the group message;

send respective request messages from the data network device to respective said active network components of the first data set, wherein each respective request message indicates a respective data network address of the respective active network component and the data network address of the medical device that sent the group message;

receive an acknowledgment message from a defined active network component, which defined active network component received the request message, which acknowledgment message indicates the data network address of the defined active network component, a port identity of a port of the defined active network component, to which the medical device is connected and the data network address of the medical device;

assign the medical device to a physical location on the basis of the received acknowledgment message from the defined active network component and the data network address of the defined active network component and of the indicated port identity assigned to the physical location of the second data set and assign the medical device to a patient data set, which identifies a patient, on the basis of the received acknowledgment message from the defined active network component and the data network address of the defined active network component and of the indicated port identity assigned to the patient data set; and provide an assignment data set, which indicates the assignment of the medical device to the assigned physical location and the assignment of the medical device to a patient data set, which identifies the patient.

10. A device in accordance with claim 9, wherein the at least one processing unit using the data network interface is further configured to send a group message from the data network device over the data network via the network interface, which group message indicates a request to medical devices to send their own respective group messages, which indicate their own respective data network addresses, wherein the sending of the group message by the data network device occurs before receiving the group message by the data network device, which has the data network address of the medical device.

11. A device in accordance with claim 9, wherein the assignment data set contains identification data of the medical device as well as, further, a data set, which identifies the assigned physical location.

12. A device in accordance with claim 11, wherein the identification data of the medical device is the data network address of the medical device.

13. A device in accordance with claim 9, wherein the provision of the assignment data set by the processing unit comprises sending a data message from the device, via the data network, to the medical device, wherein the data message contains the assignment data set.

14. A device in accordance with claim 9, wherein the provision of the assignment data set comprises sending a data message to a server unit, wherein the data message contains the assignment data set.

15. A device in accordance with claim 14, wherein the sending of the data message takes place upon receipt of a request message to the server unit.

16. A device for a data network having one or more active network components comprising a router or a managed switch or multilayer switch and one or more network connected medical devices, each of the one or more network connected medical devices having a data network address and being connected to a port of one of the active network components, the device comprising:

a data network interface connecting the data network device to the data network, the data network interface receiving and sending data network messages;

a memory unit configured with a first data set indicating data network addresses of respective active network components of the data network, and with a second data set indicating an assignment of respective tuples of active network component data network addresses and active network component port identities to respective physical locations and to an assignment of the respective tuples of active network component data network addresses and port identities to respective patient data sets, which identify patients;

a processing unit connected to the memory unit and using the data network interface and configured to:

receive a medical device group message at the data network device, which medical device group message has a data network address of a network connected medical device sending the group message;

subsequent to receipt of the medical device group message, send respective request messages from the data network device to respective said active network components of the first data set, wherein each respective request message indicates a respective data network address of the respective active network component and the data network address of the network connected medical device that sent the medical device group message;

receive an acknowledgment message from a defined active network component, which defined active network component received the request message, which acknowledgment message indicates the data network address of the defined active network component, a port identity of a port of the defined active network component, to which the network connected medical device that sent the medical device group message is connected and the data network address of the network connected medical device that sent the medical device group message;

assign the network connected medical device that sent the group message to a physical location on the basis of the second data set as well as the data network address of the defined active network component and of the indicated port identity;

provide an assignment data set, which indicates an assignment of the network connected medical device that sent the group message to the assigned physical location and also an assignment of the network connected medical device that sent the group message to a patient data set on the basis of the second data set, whereby the assignment data set includes assigned patient data, correlated with the data network address of the assigned medical device and the assigned physical location;

send a data message to the network connected medical device that sent the group message and to a server, wherein the data message contains the assignment data.

17. A device in accordance with claim 16, wherein:

the at least one processing unit, using the data network interface, is further configured to send a group message from the data network device over the data network via the network interface;

the group message sent from the data network device indicates a request to network connected medical devices to send respective medical device group messages, which indicate their own respective data network addresses;

the sending of the group message by the at least one processing unit from the data network device occurs before receiving the medical device group message by the data network device, which has the data network address of the network connected medical device that sent the group message.

\* \* \* \* \*